United States Patent
Chung et al.

(10) Patent No.: US 9,511,011 B2
(45) Date of Patent: Dec. 6, 2016

(54) TRPV1 INHIBITORY PEPTIDES AND COMPOSITION FOR SKIN-AGING PROTECTION OR WRINKLE IMPROVEMENT COMPRISING THE SAME

(71) Applicant: SNU R&DB FOUNDATION, Seoul (KR)

(72) Inventors: Jin Ho Chung, Seoul (KR); So Min Kang, Seoul (KR); Young Mee Lee, Seoul (KR); Yeon Kyung Kim, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 14/725,383

(22) Filed: May 29, 2015

(65) Prior Publication Data
US 2015/0257998 A1    Sep. 17, 2015

Related U.S. Application Data

(60) Division of application No. 13/855,022, filed on Apr. 2, 2013, now Pat. No. 9,056,889, which is a continuation of application No. PCT/KR2012/001932, filed on Mar. 16, 2012.

(51) Int. Cl.
| | |
|---|---|
| *A61K 38/08* | (2006.01) |
| *A61K 8/64* | (2006.01) |
| *A61K 35/36* | (2015.01) |
| *A61Q 19/02* | (2006.01) |
| *A61Q 19/08* | (2006.01) |
| *C07K 7/06* | (2006.01) |
| *G01N 33/50* | (2006.01) |
| *G01N 33/68* | (2006.01) |

(52) U.S. Cl.
CPC .............. *A61K 8/64* (2013.01); *A61Q 19/02* (2013.01); *A61Q 19/08* (2013.01); *C07K 7/06* (2013.01); *G01N 33/502* (2013.01); *G01N 33/5008* (2013.01); *G01N 33/6872* (2013.01); *G01N 2333/705* (2013.01)

(58) Field of Classification Search
CPC ........ A61K 8/64; A61K 35/36; A61K 38/08; A61Q 19/02; A61Q 19/08; C07K 7/06

USPC ......... 514/17.4, 18.6, 21.5, 21.6, 21.7, 21.8; 530/328, 330
See application file for complete search history.

(56) References Cited

U.S. PATENT DOCUMENTS

| | | | |
|---|---|---|---|
| 6,482,611 B1 * | 11/2002 | Cortright | C07K 14/705 435/252.3 |
| 2004/0009537 A1 | 1/2004 | Roos et al. | |
| 2008/0195328 A1 | 8/2008 | Nakata et al. | |
| 2010/0210478 A1 * | 8/2010 | Gao | B01J 19/0046 506/18 |
| 2011/0184660 A1 | 7/2011 | Nakata et al. | |

FOREIGN PATENT DOCUMENTS

| | | |
|---|---|---|
| JP | 2006-38614 A | 2/2006 |
| KR | 10-2010-0000391 A | 1/2010 |

OTHER PUBLICATIONS

SEQ ID No. 28 from 2010/0210478 same as U.S. Appl. No. 12/308,035, Aug. 2010.*
The Korean Office Action, five pages, issued on Jun. 21, 2016.
Du et al., "Melittin activates TRPV1 receptors in primary nociceptive sensory neurons via the phospholipase A2 cascade pathways", Biochemical and Biophysical Research Communications, vol. 408, No. 1, pp. 32-37, (2011).
Okada et al., "TRPV1 Involvement in Inflammatory Tissue Fibrosis in Mice", The American Journal of Pathology, vol. 178, No. 6, pp. 2654-2664, (2011).
Takita et al., "Capsaicin, A Ligand for Vanilloid Receptor-1, Transduces Suppressive Signal for Osteoclast Differentiation in Bone", Journal of Health Science, vol. 53, No. 2, pp. 240-244, (2007).
The Japanese Office Action, six pages, issued on Feb. 23, 2016.

* cited by examiner

*Primary Examiner* — Julie Ha
(74) *Attorney, Agent, or Firm* — Vorys, Sater, Seymour & Pease LLP; Mih Suhn Koh

(57) ABSTRACT

TRPV1 inhibitory peptides and a composition for skin-aging prevention and wrinkle improvement comprising the same as an active ingredient are described. The TRPV1 inhibitory peptide of the present subject matter inhibits the expressions of MMP and proinflammatory cytokines induced by UV exposure and reduces skinfold thickness and intracellular $Ca^{2+}$ influx, so that it can be effectively used as an active ingredient of the composition for skin-aging prevention, wrinkle improvement, skin-whitening, or alleviating inflammation, irritation, or pain.

16 Claims, 18 Drawing Sheets

Peptide 1. QRRPSLKSL (mouse TRPV1 499-507)

Peptide 2. QRAITILDT (mouse TRPV1 701-709)

Peptide 3. RRPSL (mouse TRPV1 500-504)

Peptide 4. RAITI (mouse TRPV1 702-706)

Peptide 1. QRRPSLKSL (mouse TRPV1 499-507)
Peptide 2. QRAITILDT (mouse TRPV1 701-709)
Peptide 3. RRPSL (mouse TRPV1 500-504)
Peptide 4. RAITI (mouse TRPV1 702-706)

```
SEQUENCE LISTING

<160> NUMBER OF SEQ ID NOS: 18

<210> SEQ ID NO 1
<211> LENGTH: 9
<212> TYPE: PRT
<213> ORGANISM: Artificial Sequence
<220> FEATURE:
<223> OTHER INFORMATION: TRPV1 inhibitory peptide 1

<400> SEQUENCE: 1

Gln Arg Arg Pro Ser Leu Lys Ser Leu
1               5

<210> SEQ ID NO 2
<211> LENGTH: 9
<212> TYPE: PRT
<213> ORGANISM: Artificial Sequence
<220> FEATURE:
<223> OTHER INFORMATION: TRPV1 inhibitory peptide 2

<400> SEQUENCE: 2

Gln Arg Ala Ile Thr Ile Leu Asp Thr
1               5

<210> SEQ ID NO 3
<211> LENGTH: 5
<212> TYPE: PRT
<213> ORGANISM: Artificial Sequence
<220> FEATURE:
<223> OTHER INFORMATION: TRPV1 inhibitory peptide 3
```

```
<400> SEQUENCE: 3

Arg Arg Pro Ser Leu
1               5

<210> SEQ ID NO 4
<211> LENGTH: 5
<212> TYPE: PRT
<213> ORGANISM: Artificial Sequence
<220> FEATURE:
<223> OTHER INFORMATION: TRPV1 inhibitory peptide 4

<400> SEQUENCE: 4

Arg Ala Ile Thr Ile
1               5

<210> SEQ ID NO 5
<211> LENGTH: 9
<212> TYPE: PRT
<213> ORGANISM: Artificial Sequence
<220> FEATURE:
<223> OTHER INFORMATION: TRPV1 inhibitory peptide 5

<400> SEQUENCE: 5

Met His Arg Gln Glu Thr Val Asp Cys
1               5

<210> SEQ ID NO 6
<211> LENGTH: 10
<212> TYPE: PRT
<213> ORGANISM: Artificial Sequence
<220> FEATURE:
<223> OTHER INFORMATION: TRPV1 inhibitory peptide 6

<400> SEQUENCE: 6

Leu Lys Lys Phe Asn Ala Arg Arg Lys Leu
1               5                   10

<210> SEQ ID NO 7
<211> LENGTH: 5
<212> TYPE: PRT
<213> ORGANISM: Artificial Sequence
<220> FEATURE:
<223> OTHER INFORMATION: TRPV1 inhibitory peptide 7

<400> SEQUENCE: 7

Arg Gln Glu Thr Val
1               5

<210> SEQ ID NO 8
<211> LENGTH: 5
<212> TYPE: PRT
<213> ORGANISM: Artificial Sequence
<220> FEATURE:
<223> OTHER INFORMATION: TRPV1 inhibitory peptide 8

<400> SEQUENCE: 8

Lys Phe Asn Ala Arg
1               5

<210> SEQ ID NO 9
<211> LENGTH: 18
<212> TYPE: DNA
<213> ORGANISM: Artificial Sequence
<220> FEATURE:
<223> OTHER INFORMATION: 36B4 forward primer

<400> SEQUENCE: 9
```

```
tgggctccaa gcagatgc                                                    18

<210> SEQ ID NO 10
<211> LENGTH: 18
<212> TYPE: DNA
<213> ORGANISM: Artificial Sequence
<220> FEATURE:
<223> OTHER INFORMATION: 36B4 reverse primer

<400> SEQUENCE: 10
ggcttcgctg gctcccac                                                    18

<210> SEQ ID NO 11
<211> LENGTH: 24
<212> TYPE: DNA
<213> ORGANISM: Artificial Sequence
<220> FEATURE:
<223> OTHER INFORMATION: MMP-1 forward primer

<400> SEQUENCE: 11
attctactga tatcggggct ttga                                             24

<210> SEQ ID NO 12
<211> LENGTH: 23
<212> TYPE: DNA
<213> ORGANISM: Artificial Sequence
<220> FEATURE:
<223> OTHER INFORMATION: MMP-1 reverse primer

<400> SEQUENCE: 12
atgtccttgg ggtatccgtg tag                                              23

<210> SEQ ID NO 13
<211> LENGTH: 20
<212> TYPE: DNA
<213> ORGANISM: Artificial Sequence
<220> FEATURE:
<223> OTHER INFORMATION: MMP-13 forward primer

<400> SEQUENCE: 13
catccatccc gtgaccttat                                                  20

<210> SEQ ID NO 14
<211> LENGTH: 20
<212> TYPE: DNA
<213> ORGANISM: Artificial Sequence
<220> FEATURE:
<223> OTHER INFORMATION: MMP-13 reverse primer

<400> SEQUENCE: 14
gcatgactct cacaatgcga                                                  20

<210> SEQ ID NO 15
<211> LENGTH: 20
<212> TYPE: DNA
<213> ORGANISM: Artificial Sequence
<220> FEATURE:
<223> OTHER INFORMATION: MMP-9 forward primer

<400> SEQUENCE: 15
ttgagtccgg cagacaatcc                                                  20

<210> SEQ ID NO 16
<211> LENGTH: 20
<212> TYPE: DNA
```

```
<213> ORGANISM: Artificial Sequence
<220> FEATURE:
<223> OTHER INFORMATION: MMP-9 reverse primer

<400> SEQUENCE: 16
ccttatccac gcgaatgacg                                            20

<210> SEQ ID NO 17
<211> LENGTH: 19
<212> TYPE: DNA
<213> ORGANISM: Artificial Sequence
<220> FEATURE:
<223> OTHER INFORMATION: procollagen forward primer

<400> SEQUENCE: 17
tcgtgaccgt gaccttgcg                                             19

<210> SEQ ID NO 18
<211> LENGTH: 20
<212> TYPE: DNA
<213> ORGANISM: Artificial Sequence
<220> FEATURE:
<223> OTHER INFORMATION: procollagen reverse primer

<400> SEQUENCE: 18
aggcacagac ggctgagtag                                            20
```

TRPV1 INHIBITORY PEPTIDES AND COMPOSITION FOR SKIN-AGING PROTECTION OR WRINKLE IMPROVEMENT COMPRISING THE SAME

The Sequence Listing submitted in text format (.txt) filed on May 29, 2015, named "SequenceListing.txt", created on Mar. 19, 2013, 3.76 KB), is incorporated herein by reference.

FIELD OF THE INVENTION

The present invention relates to a novel peptide inhibiting the activity of TRPV1 that affects the intracellular $Ca^{2+}$ influx, and a composition for skin-aging prevention, wrinkle improvement, skin-whitening, or alleviating inflammation, irritation, or pain in skin comprising the same.

DESCRIPTION OF THE RELATED ART

Skin-aging is caused by internal (natural) or external process involved in the development of wrinkles, skin sagging, and drooping. The major factor causing external aging is repetitive ultraviolet ray (UV) exposure, so the external aging is generally called 'photo-aging'. The naturally aged skin has fine wrinkles but the skin is still smooth and white, but the photo-aged skin has thick and rough wrinkles with showing pigmentation and capillary telangiectasia.

The damage in collagen which is the major structural component of skin has been known as a critical reason of skin-aging, which is observed in both naturally aged skin and photo-aged skin. Collagen damage is partly related to matrix metalloproteinase (MMP) induction. The MMP is a member of matrix-lyase family in the structural viewpoint, which plays an important role in a variety of processes such as inflammation, tumor invasion, and skin-aging. MMP level is increased by various stimuli such as UV, oxidative stress, and cytokines. UV irradiation accelerates DNA binding of activator protein-1 (AP-1) and also induces such MMPs as collagenase (MMP-1), stromelysin (MMP-3), and gelatinase (MMP-9). Once collagen is decomposed by MMP-1, it is further decomposed continuously by MMP-3 and MMP-9.

According to the recent report, calcium can regulate MMP expression and activity. That is, calcium is involved in the regulation of MMP-12 activation and the increased extracellular calcium induces MMP-9 gene expression in human keratinocytes. In the meantime, the suppression of $Ca^{2+}$ influx reduces the level of MMP-1 mRNA. The regulation of intracellular $Ca^{2+}$ level can change MMP-1 secretion in keratinocytes.

TRPV1 (transient receptor potential vanilloid type 1) is a member of calcium permeable non-selective cation channel family. The activation of TRPV1 induces $Ca^{2+}$ influx and is suppressed by a specific antagonist such as capsazepine. TRPV1 is directly activated by capsaicin, heat, low pH, bradykinin, $PGE_2$, or ATP. Considering such activation condition, it is suggested that TRPV1 is a primary biological sensor for thermo-chemical stimulus and tissue damage. It has been reported that TRPV1 is distributed in various tissues including those in the brain and kidney, and airway epithelial cells, and epidermal keratinocytes, etc. Capsaicin stimulus increases intracellular $Ca^{2+}$ level in keratinocytes, which is suppressed by capsazepine.

The role of TRPV1 in the MMP-1 expression induced by heat in epidermal cells was once reported. UV is a critical factor inducing MMP expression and skin-aging. According to the previous reports made by the present inventors, $Ca^{2+}$ influx induced by TRPV1 is closely related to MMP-1 expression induced by UV and $Ca^{2+}$ dependent protein kinase C (PKC) is involved in the signal transduction, suggesting that epidermal TRPV1 is functioning as a sensor for harmful stimulus like UV. Therefore, TRPV1 can be a target for the prevention of skin photo-aging caused by UV exposure. It is necessary therefore to develop a novel TRPV1 activity inhibitor in order to prevent skin-aging.

SUMMARY OF THE INVENTION

It is an object of the present invention to provide a TRPV1 inhibitory peptide and a composition for skin-aging prevention, wrinkle improvement, skin-whitening, or alleviating inflammation, irritation, or pain in skin comprising the same.

To achieve the above object, the present invention provides peptides represented by SEQ. ID. NO: 1~SEQ. ID. NO: 8.

In a preferred embodiment of the present invention, the said peptides are identified as novel TRPV1 activation inhibitory peptides.

The said TRPV1 is a non-specific cation channel belonging to TRP family, which is activated by capsaicin that is the ingredient of pepper giving hot taste and is a membrane protein that is introduced to form membrane potential by cation influx to transmit a stimulus to nerve system. The activation of TRPV1 is regulated by different pathways, which is exemplified by phosphorylation/dephosphorylation including PKA, PKC, $Ca^{2+}$/calmodulin-dependent protein kinase (CaMK), and Src kinase. In addition to that, the activation of TRPV1 is also regulated by post-transcriptional regulation system. The regulation process of TRPV1 includes protein-protein interaction, but only a few proteins involved in the interaction with TRPV1 have been known.

In a preferred embodiment of the present invention, the present inventors tried to find TRPV1 activation inhibitors applicable for the treatment of disease targeting TRPV1, and as a result, the inventors identified novel peptides represented by SEQ. ID. NO: 1~SEQ. ID. NO: 8. These peptides are the peptide sequences based on the phosphorylated amino acid of TRPV1 or the peptides capable of inhibiting CaMK active site affecting intracellular $Ca^{2+}$ influx triggered by TRPV1 activation. Since the effective inhibition of TRPV1 activation has been confirmed in this invention, the novel peptides can be effectively used as TRPV1 activation inhibitors.

The present invention also provides a cosmetic composition for skin-aging prevention or wrinkle improvement comprising one or more peptides selected from the group consisting of the peptides represented by SEQ. ID. NO: 1~SEQ. ID. NO: 8 as active ingredients.

The prevention of skin-aging herein indicates the inhibition of skin-aging caused by photo-aging or natural aging, but preferably indicates the inhibition of skin-aging caused by UV induced photo-aging.

In a preferred embodiment of the present invention, the skin wrinkles are the ones caused by photo-aging or natural aging, but preferably the ones induced by photo-aging, and more preferably the ones induced by UV exposure, but not always limited thereto. The said skin-aging and wrinkles herein are induced by TRPV1 activation, but not always limited thereto.

The concentration of the said peptide in the cosmetic composition is preferably 0.001~20 mM, and more preferably 0.01~10 mM, but not always limited thereto. If the concentration of the said peptide is less than 0.001 mM, the inhibitory effect on TRPV1 is not guaranteed, so that anti-aging and skin wrinkle improvement effect cannot be expected either. Even though the concentration of the peptide is more than 20 mM, the effect is not getting any bigger, indicating that production efficiency decreases.

The peptides of the present invention can be produced by the general chemical synthesis, for example by solid-phase peptide synthesis, or produced by the conventional method in which microorganisms are transfected by the recombinant vector comprising the nucleic acid encoding the said peptide and then the peptide expressed in the cultured microorganism is recovered and purified, but not always limited thereto.

The cosmetic composition of the present invention can include, in addition to the said peptide, any conventional ingredients generally used in cosmetics, for example such additives and carriers as anti-oxidants, stabilizers, solubilizers, vitamins, pigments and flavors, but not always limited thereto.

The cosmetic composition of the present invention can be formulated in any form that can be accepted in the art, which is exemplified by liquid, suspension, emulsion, paste, gel, cream, lotion, powder, soap, surfactant-containing cleansing, oil, powdered foundation, emulsion foundation, and spray. Particularly, the cosmetic composition of the present invention can be prepared in the form of toner, essence, lotion, cream, pack, gel, ointment, patch, or spray.

In the case that the cosmetic composition is formulated as paste, cream or gel, a proper carrier can be selected from the group consisting of animal oil, vegetable oil, wax, paraffin, starch, tracanth, cellulose derivative, polyethylene glycol, silicon, bentonite, silica, talk and zinc oxide. In the case that the cosmetic composition is formulated as powder or spray, a proper carrier can be selected from the group consisting of lactose, talc, silica, aluminum hydroxide, calcium silicate and polyamide powder, and in particular if the composition of the present invention is formulated as spray, a propellant such as chlorofluorohydrocarbon, propane/butane or dimethyl ether can be additionally included.

In the case that the cosmetic composition is formulated as liquid or emulsion, a proper carrier can be selected from the group consisting of solvent, solubilizer and emulsifier, which is exemplified by water, ethanol, isopropanol, ethyl carbonate, ethyl acetate, benzyl alcohol, benzyl benzoate, propylene glycol, 1,3-butyl glycol oil, glycerol aliphatic ester, polyethylene glycol and fatty acid ester of sorbitan.

In the case that the cosmetic composition is formulated as suspension, the proper carrier can be selected from the group consisting of liquid diluent such as water, ethanol or propylene glycol; suspending agent such as ethoxylated isostearyl alcohol, polyoxyethylene sorbitol ester and polyoxyethylene sorbitan ester; microcrystalline cellulose; aluminum methahydroxide; bentonite; agar; and tragacanth. In the case that the cosmetic composition is formulated as surfactant-containing cleansing, a proper carrier can be selected from the group consisting of aliphatic alcohol sulfate, aliphatic alcohol ether sulfate, sulfosuccinic monoester, isethionate, imidazolinum derivative, methyltaurate, sarcosinate, fatty acid amide ether sulfate, alkyl amidobetain, aliphatic alcohol, fatty acid glyceride, fatty acid diethanolamide, vegetable oil, lanolin derivative and ethoxylated glycerol fatty acid ester.

It is well known that the expression and activation of TRPV1 is increased after UV exposure, and accordingly intracellular $Ca^{2+}$ influx is induced thereby. CaMK also affects $Ca^{2+}$ influx. Skin-aging is induced by the increase of MMP-1, the ECM formation related matrix protein, and other cytokines caused by UV exposure.

The said TRPV1 is involved in the regulation of the proliferation and differentiation of skin cells. TRPV1 mediated calcium influx in cultured human keratinocytes suppresses cell proliferation and induces apoptosis. In particular, capsaicin or heat mediated TRPV1 activation is known to change the formation pattern of epidermal permeability barrier of human skin.

In a preferred embodiment of the present invention, the present inventors investigated to develop a novel inhibitor that could suppress the activity of TRPV1. As a result, novel TRPV1 inhibitory peptides (peptide 1: QRRPSLKSL, peptide 2: QRAITILDT, peptide 3: RRPSL, peptide 4: RAITI, peptide 5: MHRQETVDC, peptide 6: LKKFNARRKL, peptide 7: RQETV, and peptide 8: KFNAR) were identified. The present inventors studied further to confirm the effect of those peptides on skin-aging prevention and wrinkle improvement.

In a preferred embodiment of the present invention, the said peptides were treated to HaCaT cells, the human keratinocyte cell line, and as a result, MMP-1 expression induced by UV exposure was decreased (see FIG. 1a and FIG. 1b). In addition, the expressions of pro-inflammatory cytokines such as IL-1β, IL-6, IL-8, and TNF-α were also inhibited (see FIG. 2a~FIG. 2h). Therefore, it was confirmed that the peptides of the present invention could inhibit the abnormal intracellular increase induced by UV irradiation. Unlike in the control group treated with capsaicin, the TRPV1 activation inducer, alone, in the experimental group treated with the peptides of the present invention after being treated with capsaicin, it was confirmed that the intracellular $Ca^{2+}$ influx induced by capsaicin was suppressed by the peptides (see FIG. 3).

To investigate the in vivo effect of the TRPV1 inhibitory peptides of the present invention, nude mouse skin was irradiated with UV, followed by the treatment of the said peptides (see FIG. 4). As a result, those peptides reduced the skinfold thickness increased by UV exposure dose-dependently (see FIG. 5 and FIG. 9) and also reduced the expressions of MMP-13 and MMP-9 (see FIG. 6 and FIG. 7). In the meantime, the expression of procollagen, the precursor material of collagen, was increased (see FIG. 8). In addition, the peptides of the present invention suppressed apoptosis induced by UV exposure (see FIG. 10). The novel peptides of the present invention were confirmed to inhibit the activation of TRPV1 involved in skin-aging, and accordingly have the effect of suppressing UV induced skin-aging, and also inhibit the expression and activation of MMP but increase the expression of procollagen to bring the effect of improving skin wrinkles and elasticity. Therefore, the peptides of the present invention can be effectively used as active ingredients for the cosmetic composition for the prevention of skin-aging and the improvement of skin wrinkles.

The present invention also provides a pharmaceutical composition for the prevention of skin-aging or the improvement of wrinkles comprising one or more peptides selected from the group consisting of the peptides represented by SEQ. ID. NO: 1~SEQ. ID. NO: 8 as active ingredients.

In a preferred embodiment of the present invention, the said skin-aging can be either natural aging or photo-aging, and photo-aging is more preferred, and particularly photo-aging caused by UV exposure is most preferred, but not always limited thereto.

The concentration of the said peptide in the pharmaceutical composition is preferably 0.001~20 mM, and more preferably 0.01~10 mM, but not always limited thereto. If the concentration of the peptide is less than 0.001 mM, skin-aging prevention or wrinkle improvement effect is not guaranteed. In the meantime, if the concentration of the peptide is more than 20 mM, the excessive peptides become just waste.

The administration of the TRPV1 inhibitory peptides of the present invention can suppress the expressions of MMP and pro-inflammatory cytokines induced by UV exposure in vivo and in human keratinocytes, reduce skinfold thickness and apoptosis, but increase the expression of procollagen reduced by UV exposure, so that the peptides of the present invention can be effectively used as active ingredients for the pharmaceutical composition for the prevention of skin-aging and the improvement of wrinkles.

The present invention also provides a pharmaceutical composition for skin whitening comprising one or more peptides selected from the group consisting of the peptides represented by SEQ. ID. NO: 1~SEQ. ID. NO: 8 as active ingredients.

The concentration of the said peptide in the pharmaceutical composition is preferably 0.001~20 mM, and more preferably 0.01~10 mM, but not always limited thereto. If the concentration of the peptide is less than 0.001 mM, skin whitening effect is not guaranteed. On the contrary, if the concentration is more than 20 mM, skin whitening effect is still not increased no matter how much more peptides are used, suggesting that it is not efficient.

In a preferred embodiment of the present invention, it was confirmed that the TRPV1 inhibitory peptides of the present invention could inhibit UV induced MMP expression in vivo and in human keratinocytes, reduce skinfold thickness and apoptosis, but increase the expression of procollagen. Since the TRPV1 inhibitory peptides have the improvement effect on skin darkness caused by UV exposure, indicating skin whitening effect, by increasing the proliferation and regeneration of keratinocytes, they can be effectively used as active ingredients for the pharmaceutical composition for skin whitening.

The present invention also provides a pharmaceutical composition for alleviating inflammation, irritation, or pain, comprising one or more peptides selected from the group consisting of the peptides each represented by SEQ. ID. NO: 1~SEQ. ID. NO: 8 as active ingredients.

The concentration of the peptide included in the pharmaceutical composition of the present invention is preferably 0.001~20 mM, and more preferably 0.01~10 mM, but not always limited thereto.

The said inflammation, irritation, and pain can be induced by such stimulus as UV exposure, but not always limited thereto.

In a preferred embodiment of the present invention, to confirm the anti-inflammatory activity of the TRPV1 inhibitory peptide of the invention, the inhibitory effect of the TRPV1 inhibitory peptide on the proinflammatory cytokines induced by UV exposure in human keratinocytes and in vivo was investigated. As a result, the expressions of the proinflammatory cytokines such as IL-1β, IL-6, IL-8, and TNF-α were significantly reduced (see FIG. 2a~FIG. 2h). It has also been reported that TRPV1 induces inflammation under the conditions of various diseases and damages. Particularly, TRPV1 is activated by capsaicin in human epithelium and hair follicle originated keratinocytes and then accelerates the secretions of proinflammatory cytokines, proving that TRPV1 is related with inflammation. In TRPV1 knockout mouse, threshold against heat was increased and decreased tissue swelling was observed in arthritis (Pharmacology and Therapeutics 2010; 125:181.95, Science 2000; 288:306.13, Arthritis and Rheumatism 2005; 52:3248.56).

In previous studies, it was confirmed that TRPV1 played an important role in pain delivery pathway. That is, once TRPV1 is activated by a pain mediator, cations are influxed in through TRPV1, the cation channel, and thus pain is delivered to the CNS by active potential. Therefore, studies have been targeting TRPV1 as an important target for the development of a pain killer and an anti-inflammatory agent (Journal of the Korea Academia-Industrial cooperation Society, 2011, pp. 3096-3102).

In addition, TRPV1 is involved in the development of skin irritation, which is precisely mediated by irritation-specific subpopulation of sensory neurons that express TRPV1 (J. Clin. Invest. 116, 1174-1186, 2006, Biochim. Biophys. Acta 1772, 1004-1021, 2007). TRPV1 is expressed not only in neurons but also in human skin, and this expression is increased especially in epithelium keratinocytes of patients with prurigo nodularis.

Therefore, the TRPV1 inhibitory peptide of the present invention can be used to improve inflammation, irritation, or pain induced by the increased TRPV1 activity by inhibiting the activity of TRPV1. That is, the TRPV1 inhibitory peptide can be effectively used as an active ingredient of a pharmaceutical composition for alleviating inflammation, irritation, or pain.

The pharmaceutical composition of the present invention can be administered orally or parenterally. Particularly, the composition can be administered by oral, intravenous, intramuscular, arterial, transdermal, hypodermic, intraperitoneal, intranasal, intraintestinal, local, sublingual, or intrarectal administration, but not always limited thereto. The parenteral administration herein includes hypodermic, intradermal, intravenous, intramuscular, or intralesional injection.

The composition of the present invention can include, in addition to the TRPV1 inhibitory peptide, one or more effective ingredients having the same or similar function to the TRPV1 inhibitory peptide. The composition of the present invention can be formulated for oral administration, for example powders, granules, tablets, capsules, suspensions, emulsions, and syrups, and for parenteral administration, for example external use, suppositories and sterile injections, etc.

Solid formulations for oral administration are powders, granules, tablets, capsules, soft capsules, and pills. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. For formulations for parenteral administration, powders, granules, tablets, capsules, sterilized suspensions, liquids, water-insoluble excipients, suspensions, emulsions, syrups, suppositories, external use such as aerosols and sterilized injections can be prepared by the conventional method, and preferably skin external pharmaceutical compositions such as creams, gels, patches, sprays, ointments, plasters, lotions, liniments, pastes or cataplasms can be prepared, but not always limited thereto. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc, but not always limited thereto.

The composition herein can additionally contain preservatives, stabilizers, wettable powders or emulsifiers, salts or buffers for the regulation of osmotic pressure, and other therapeutically useful materials, and the composition can be formulated by the conventional mixing, granulating or coating method.

The pharmaceutical composition of the present invention can be adjusted by considering individual age, weight, health condition, gender, administration time and pathway, excretion, drug combination, and severity of specific disease, etc.

When the pharmaceutical composition comprising the said peptide of the present invention as an active ingredient is formulated as unit dosage, the concentration of the peptide included as an active ingredient in the composition is preferably 0.01~1,500 mg/unit. The effective dosage for adult is preferably 1~500 mg per day, which can be adjusted by administration frequency and strength, but not always limited thereto. For intramuscular or intravenous administration, one day dosage for adult is preferably 5~300 mg in total, but higher dosage might be more preferred for some patients.

The pharmaceutical composition of the present invention can be administered alone or together with surgical operation, hormone therapy, chemo-therapy and biological regulators.

The present invention also provides a method for skin-aging prevention or wrinkle improvement comprising the step of treating or administering a pharmaceutically effective dose of one or more peptides selected from the group consisting of the peptides each represented by SEQ. ID. NO: 1~SEQ. ID. NO: 8 to a subject.

The present invention also provides a method for skin whitening comprising the step of treating or administering a pharmaceutically effective dose of one or more peptides selected from the group consisting of the peptides each represented by SEQ. ID. NO: 1~SEQ. ID. NO: 8 to a subject.

The present invention also provides a method for alleviating inflammation, irritation, or pain comprising the step of treating or administering a pharmaceutically effective dose of one or more peptides selected from the group consisting of the peptides each represented by SEQ. ID. NO: 1~SEQ. ID. NO: 8 to a subject.

The pharmaceutically effective dose herein is 0.0001~100 mg/kg, and more preferably 0.001~10 mg/kg, but not always limited thereto. The dose for the treatment or administration can be determined by considering weight, age, gender, health condition, and diet of a patient, administration period and pathway, excretion rate, and severity of disease, etc. The treatment or administration frequency can be once a day or a few times a day.

The applicable subject of the present invention is a vertebrate, preferably a mammal, more preferably a test animal such as rat, rabbit, guinea pig, hamster, dog and cat, and most preferably an anthropoid such as chimpanzee and gorilla.

The treatment or administration method is application, and oral or parenteral administration. The parenteral administration is exemplified by intraperitoneal injection, intrarectal administration, hypodermic injection, intravenous injection, intramuscular injection, intrauterine injection, intracerebroventricular injection, and intrathoracic injection.

The inflammation herein is preferably selected from the group consisting of dermatitis, allergy, atopy, asthma, conjunctivitis, periodontitis, rhinitis, otitis media, laryngopharyngitis, tonsillitis, pneumonia, gastric ulcer, gastritis, Crohn's disease, colitis, hemorrhoid, gout, ankylosing spondylitis, rheumatic fever, lupus, fibromyalgia, psoriatic arthritis, osteoarthritis, rheumatic arthritis, periarthritis of shoulder, tendonitis, tenosynovitis, peritendinitis, myositis, hepatitis, cystitis, nephritis, Sjogren's syndrome, multiple sclerosis, and acute and chronic inflammatory diseases, but not always limited thereto.

Therefore, the TRPV1 inhibitory peptide of the present invention can be effectively used for the alleviation and improvement of skin-aging and wrinkles, the diseases induced by TRPV1 activation, for skin whitening, and for alleviating inflammation, irritation, and pain, since the said peptide is effective in suppressing TRPV1 activity.

The present invention also provides a screening method of a candidate material for skin-aging prevention and wrinkle improvement comprising the following steps:
1) treating test materials to TRPV1 protein; and
2) selecting test materials able to reduce TRPV1 protein activity by measuring the activities of TRPV1 proteins of the experimental group treated with the test material and the control group not treated with the said test material.

In addition, the present invention provides a screening method using one or more peptides selected from the group consisting of those peptides represented by SEQ. ID. NO: 1~SEQ. ID. NO: 8.

Particularly, the present invention provides a screening method of a TRPV1 inhibitor comprising the following steps:
1) constructing a transformant by transfecting host cells with a plasmid containing polynucleotide encoding TRPV1;
2) treating the transformant with TRPV1 specific activator and TRPV1 inhibitor candidate materials (experimental group), and treating the transformant with the said TRPV1 specific activator and one of peptides selected from the group consisting of those peptides represented by SEQ. ID. NO: 1~SEQ. ID. NO: 8 (control group);
3) measuring the activities of TRPV1 ion channels of the experimental group and the control group of step 2); and,
4) comparing the results of both groups of step 3) and selecting TRPV1 inhibitor candidate materials demonstrating lower or similar TRPV1 ion channel activity to that of the control.

The present invention also provides a screening method of a candidate material for skin-aging prevention and wrinkle improvement comprising the following steps:
1) constructing a transformant by transfecting host cells with a plasmid containing polynucleotide encoding TRPV1;
2) treating the transformant with TRPV1 specific activator and test materials (experimental group), and treating the transformant with the said TRPV1 specific activator and one of peptides selected from the group consisting of those peptides represented by SEQ. ID. NO: 1~SEQ. ID. NO: 8 (control group);
3) measuring the activities of TRPV1 ion channels of the experimental group and the control group of step 2); and,
4) comparing the results of both groups of step 3) and selecting test materials demonstrating lower or similar TRPV1 ion channel activity to that of the control.

In a preferred embodiment of the present invention, the host cell of step 1) can be human keratinocyte cell line and is more preferably HaCaT cell line, but not always limited thereto, and any cell line that can be used for the study of ion channel activation and the high-throughput screening of the inhibitor is available.

In the above method, the TRPV1 specific activator of step 2) is preferably UV or capsaicin, and the TRPV1 inhibitory peptides of the present invention represented by SEQ. ID. NO: 1~NO: 8 are preferably treated at the concentration of 0.001~20 mM and more preferably treated at the concentration of 0.01~10 mM, but not always limited thereto.

The candidate material of step 2) can be natural compounds, synthetic compounds, RNA, DNA, polypeptides, enzymes, proteins, ligands, antibodies, antigens, metabolites of bacteria or fungi, or bioactive molecules.

The measurement of TRPV1 ion channel activity of step 3) can be performed by calcium imaging, but not always limited thereto, and any method that can confirm TRPV1 activity can be used.

The peptides represented by SEQ. ID. NO: 1~SEQ. ID. NO: 8 of the present invention can inhibit TRPV1 activity increased by UV or capsaicin known as TRPV1 activator, and demonstrate the improving effect on skin-aging and wrinkles caused by TRPV1 activation in animal model. Therefore, screening of candidates for preventing skin-aging or wrinkles caused by TRPV1 activation can be achieved by selecting TRPV1 activity inhibitor and test materials demonstrating similar or higher inhibitory effect on TRPV1 activation, compared with those peptides represented by SEQ. ID. NO: 1~SEQ. ID. NO: 8.

Advantageous Effect

As explained hereinbefore, the present invention relates to a novel peptide having skin-aging prevention and wrinkle improvement effects. The said peptide suppresses the expressions of MMP and proinflammatory cytokines induced by UV exposure in human keratinocytes and in vivo, reduces skinfold thickness, and inhibits apoptosis, but increases the expression of procollagen reduced by UV exposure. Therefore, the peptide of the present invention is very effective as an active ingredient for the composition for the prevention of skin-aging and the improvement of skin-aging mediated wrinkles and elasticity.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1A:
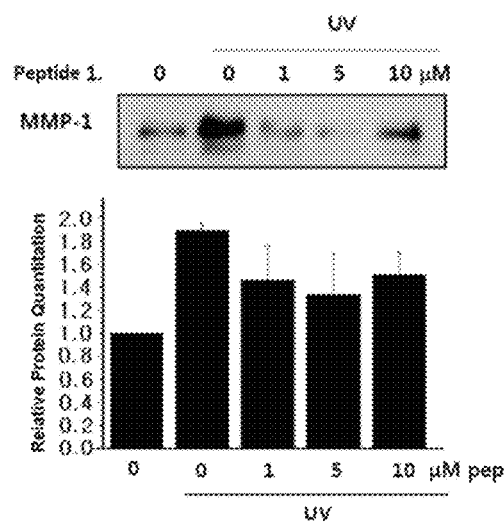
FIG. 1a and FIG. 1b are diagrams illustrating the changes of MMP-1 expression induced by UV by TRPV1 inhibitory peptide.
Figure 1A:
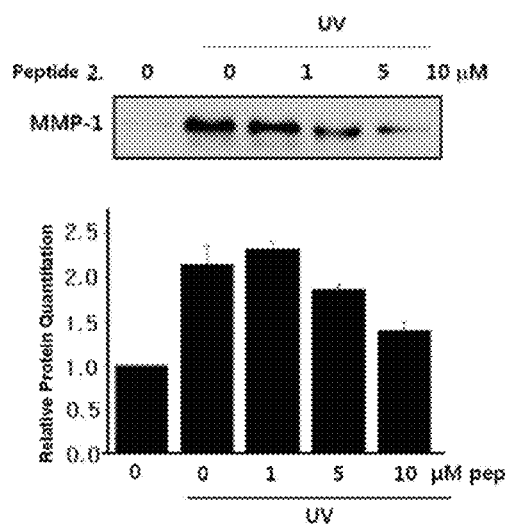
Figure 1A:
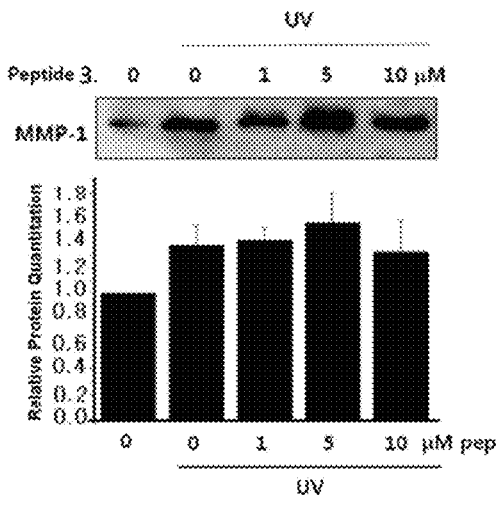
Figure 1A:
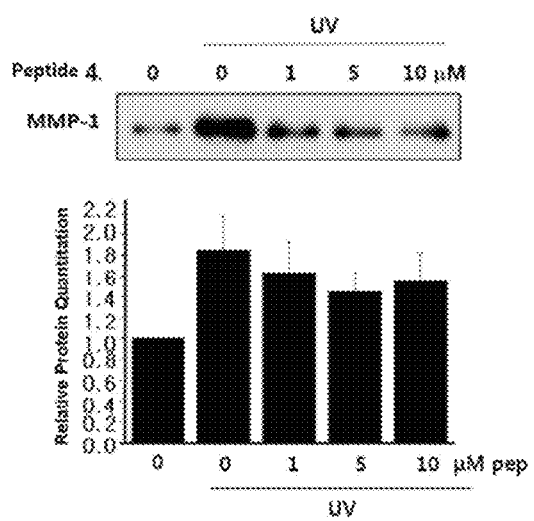

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Preparation of Novel TRPV1 Inhibitory Peptide

Novel TRPV1 inhibitory peptide sequences were synthesized [Peptron (www.peptron.com)], and the peptides were dissolved in carrier (ethanol:polyethylenglycol (PEG)=3:7) at the concentration of 1 M by calculating the concentration of each peptide according to the molecular weight thereof.

As a result, novel peptide 1: QRRPSLKSL (SEQ. ID. NO: 1), peptide 2: QRAITILDT (SEQ. ID. NO: 2), peptide 3: RRPSL (SEQ. ID. NO: 3), peptide 4: RAITI (SEQ. ID. NO: 4), peptide 5: MHRQETVDC (SEQ. ID. NO: 5), peptide 6: LKKFNARRKL (SEQ. ID. NO: 6), peptide 7: RQETV (SEQ. ID. NO: 7), and peptide 8: KFNAR (SEQ. ID. NO: 8) were obtained.

EXAMPLE 2

Human Keratinocyte Culture and Peptide Treatment

<2-1> Human Keratinocyte Culture

The immortalized human keratinocyte cell line, HaCaT, was cultured in DMEM (Dulbecco's modified Eagle's media) supplemented with glutamine (2 mM), penicillin (400 U/ml), streptomycin (50 mg/ml), and 10% FBS at 37° C. in a humidified atmosphere containing 5% $CO_2$. For the peptide treatment, the cells were cultured to 80% confluence and then maintained in culture media without FBS for 24 hours. Upon completion of the culture, the cells were washed with phosphate buffered saline (PBS) and then treated with each peptide prepared in Example <1>.

<2-2> UV Irradiation

In the Western blot and real-time RT-PCR experiments, the HaCaT cells treated with each peptide in Example <2-1> 30 minutes earlier were irradiated with a Philips TL 20W/12 RS fluorescent sun lamp with an emission spectrum ranging between 275 and 380 nm (peak, 310~315 nm). A Kodacel filter (TA401/407; Kodak) was used to block UVC, which has wavelengths of <290 nm. The UV strength was measured using a Waldmann UV meter. After UV irradiation, the cell culture medium was replaced with fresh FBS-free medium. After further culture, each peptide prepared in <Example 1> was added to the medium.

EXAMPLE 3

Confirmation of Inhibitory Activity of TRPV1 Inhibitory Peptide on UV-Induced Expressions of MMP-1 and Proinflammatory Cytokines <3-1> Confirmation of MMP-1 Expression by Western Blotting In order to determine the amounts of MMP-1 secreted into the culture media, equal aliquots of conditioned culture media from an equal number of cells were fractionated by 10% SDS-PAGE, transferred to a Hybond ECL membrane (Amersham Biosciences, Buckinghamshire, England), and analyzed by Western blotting with a rabbit monoclonal antibody against MMP-1 (Lab Frontier) by enhanced chemiluminescence (Amersham Biosciences). The signal strengths were quantified using a densitometric program (TINA; Raytest Isotopenme b gerate, Straubenhardt, Germany).

Figure 1B:
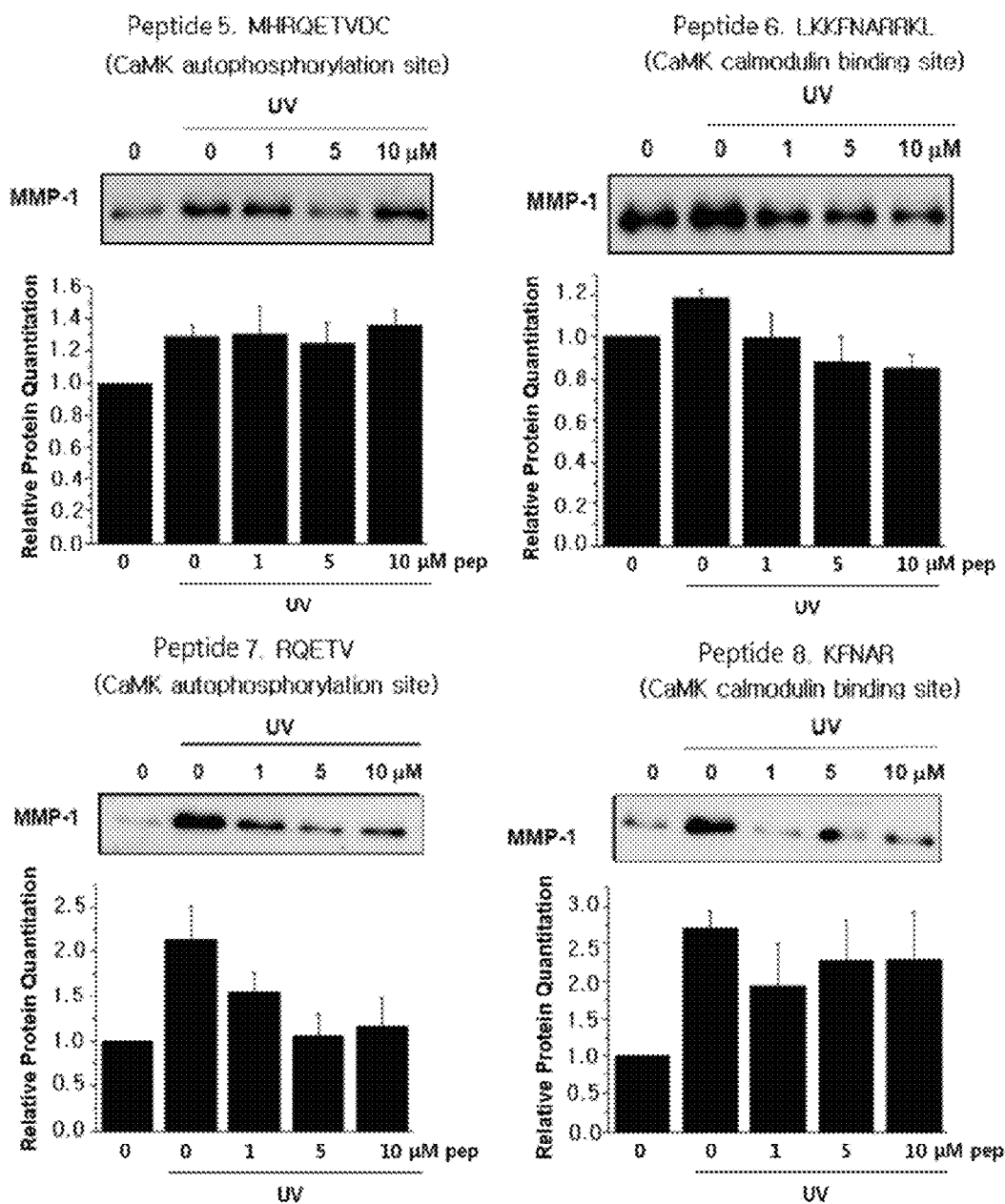
Figure 2A:
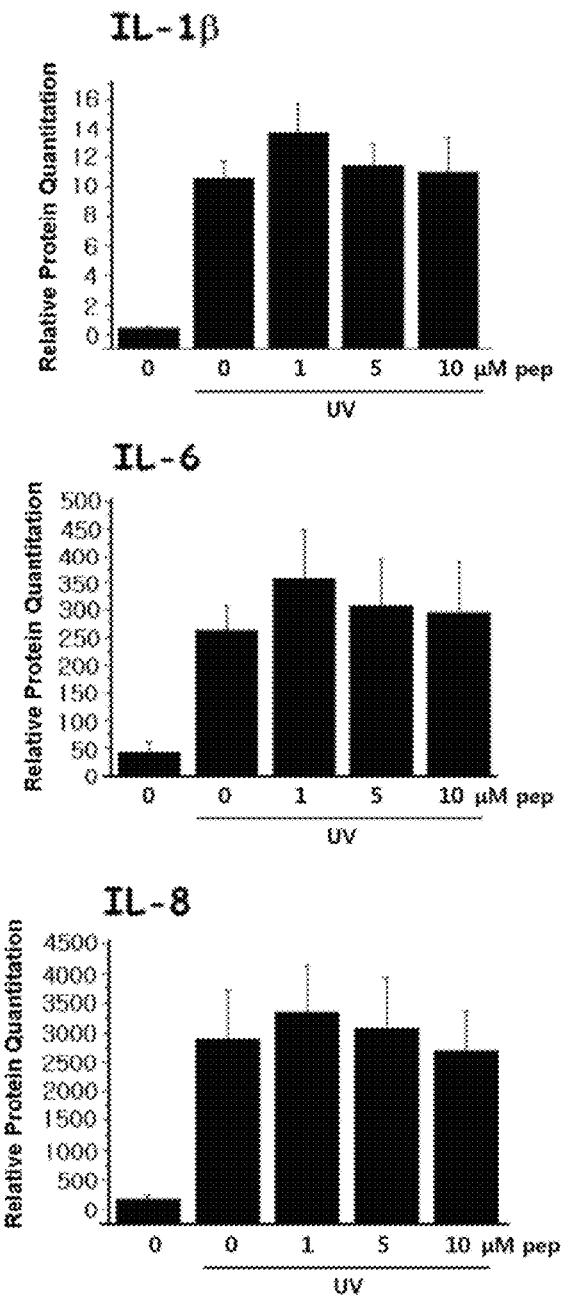
FIG. 2a~FIG. 2h are diagrams illustrating the changes of proinflammatory cytokine expression induced by UV by TRPV1 inhibitory peptide.
Figure 2B:
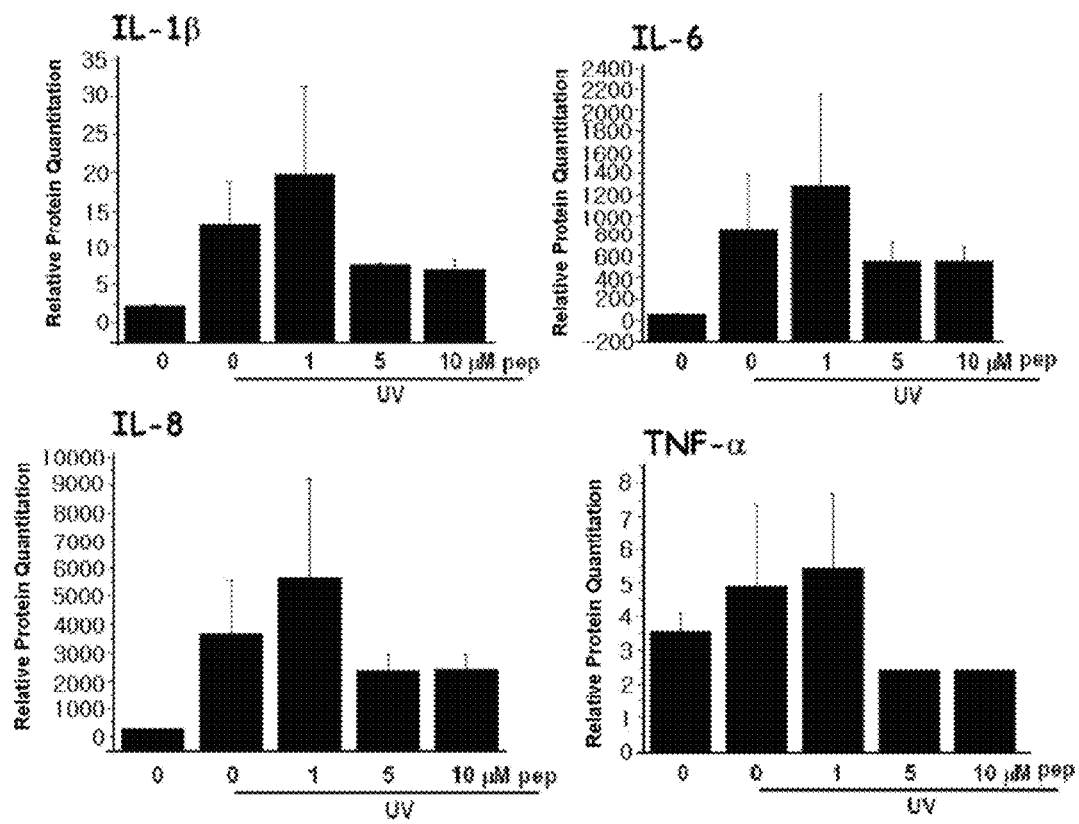
Figure 2C:
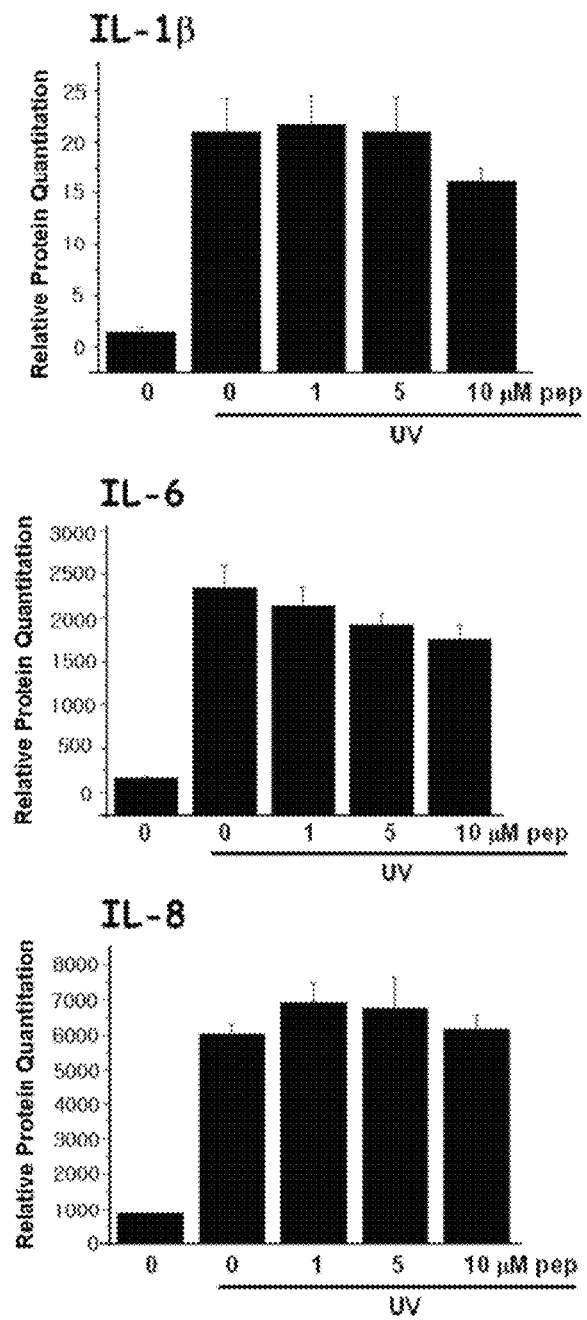
Figure 2D:
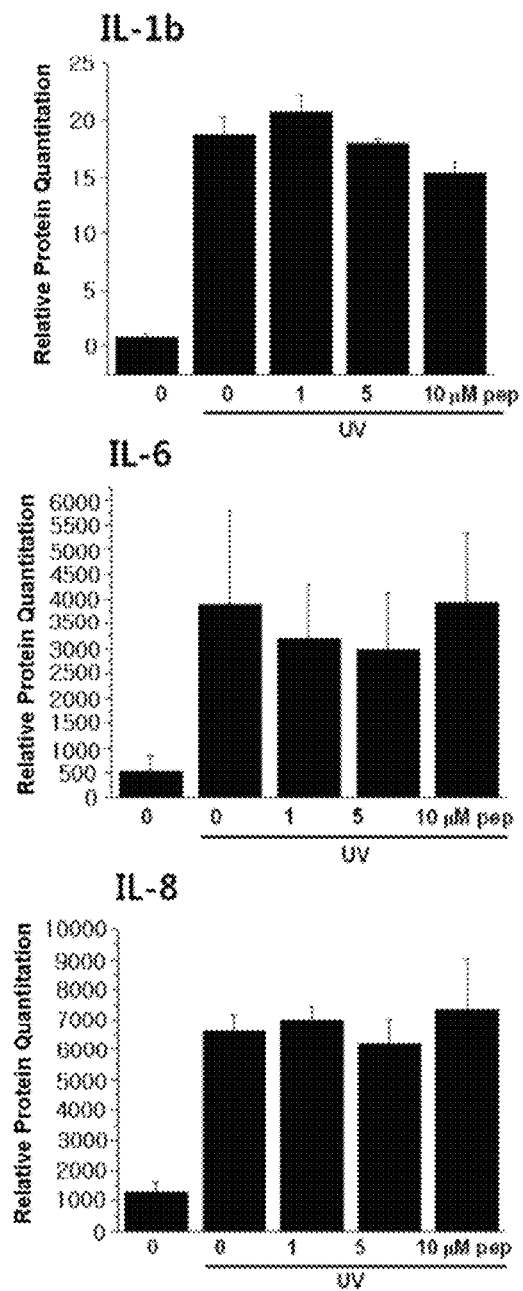
Figure 2E:
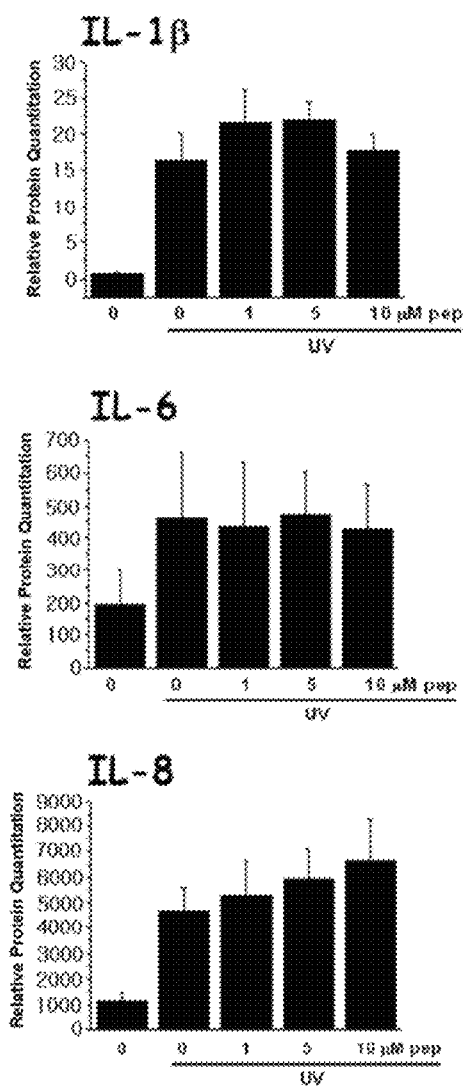
Figure 2F:
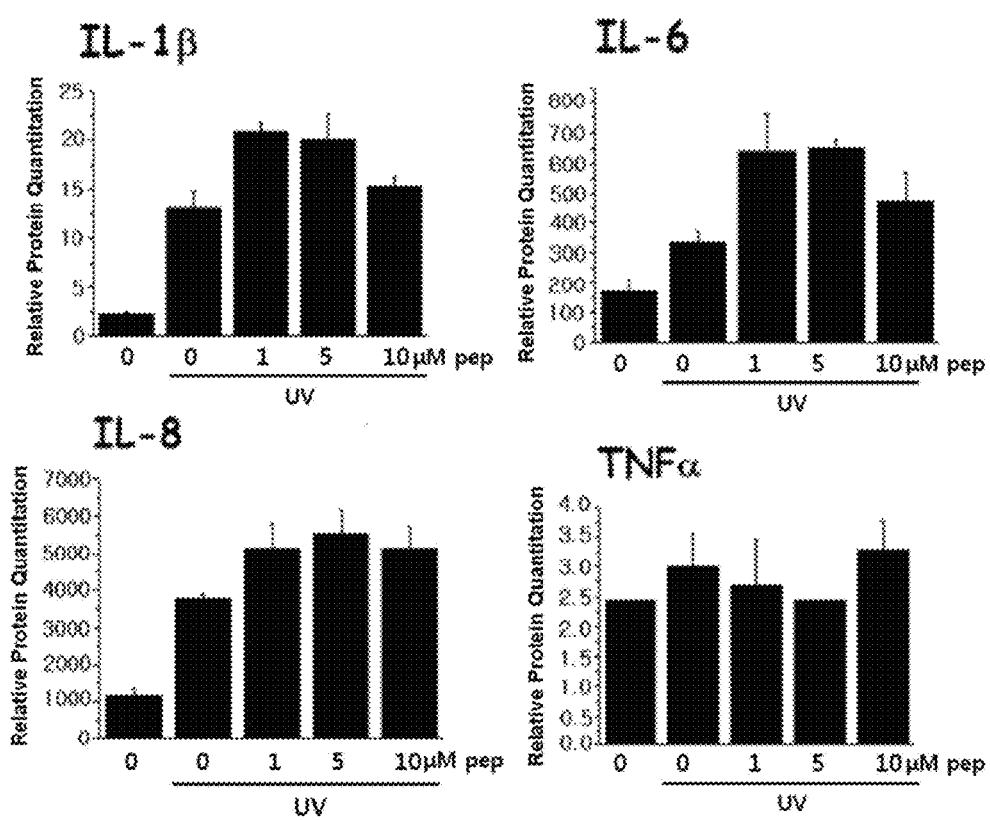
Figure 2G:
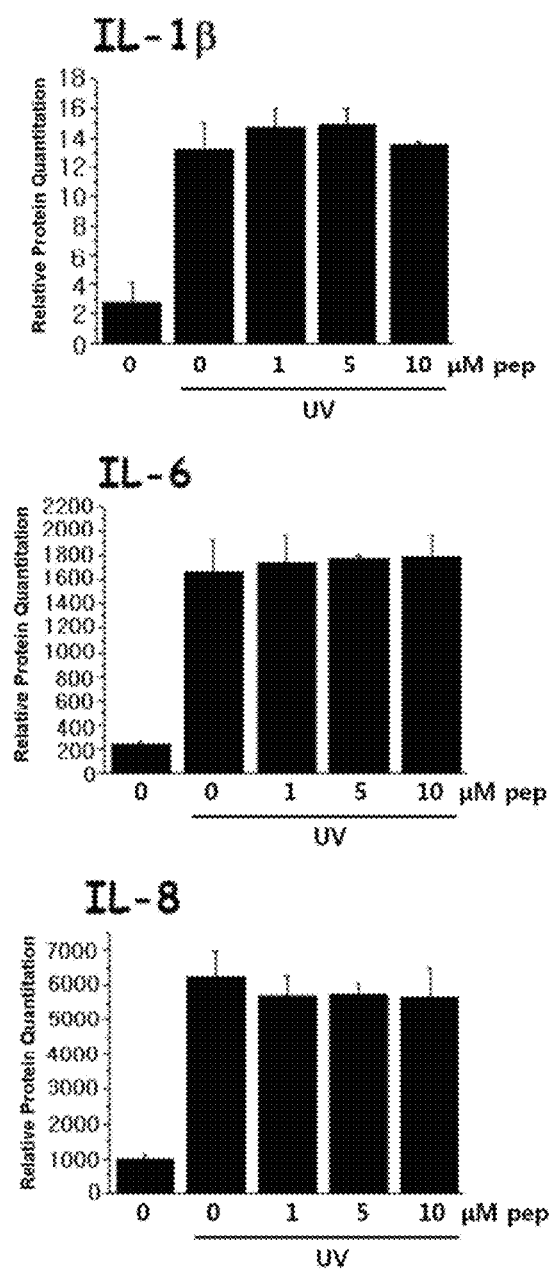
Figure 2H:
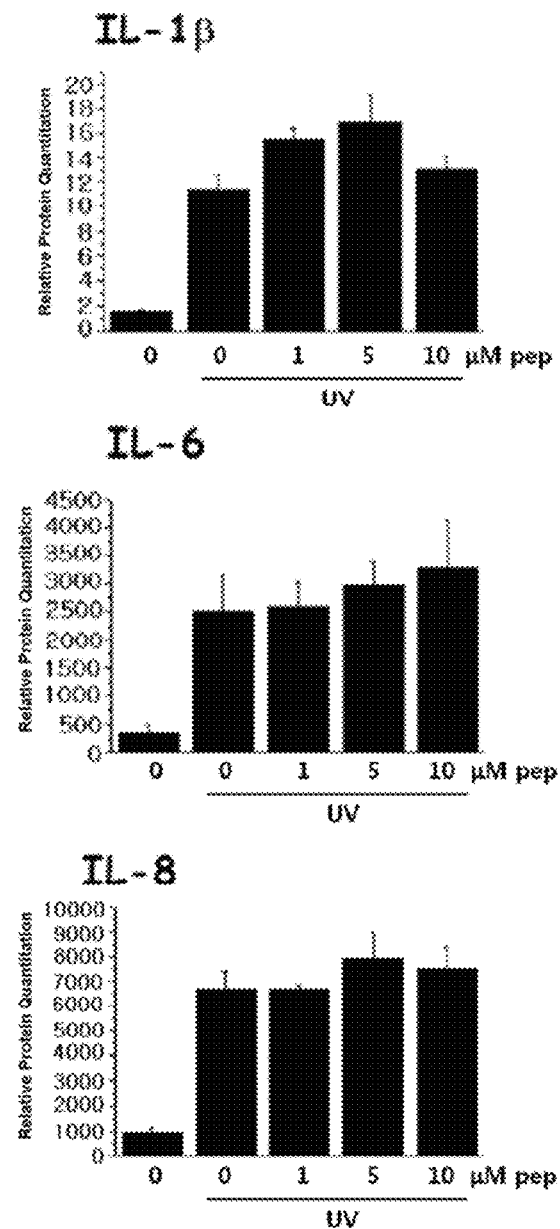

As a result, MMP-1 expression was increased in the UV-irradiated group, compared with the UV-non-irradiated group. In the group irradiated with UV and treated with the peptide, MMP-1 expression induced by UV was significantly decreased the peptide dose-dependently (FIG. 1a and FIG. 1b).

<3-2> Confirmation of MMP-1 Gene Expression by qRT-PCR

To confirm the expression of MMP-1 mRNA, total RNA was extracted from HaCaT cells using Trizol reagent according to the manufacturer's protocol (Life Technologies, Rockville, Md.). The isolated RNA samples were electrophoresed in 1% agarose gels to assess the quality and quantity. One microgram of the total RNA was used in a 20 µl reaction volume for first-strand cDNA synthesis using a first-strand cDNA synthesis kit for RT-PCR, according to the manufacturer's instructions (MBI Fermentas, Vilnius, Lithuania). For quantitative estimation of MMP-1 mRNA expression, PCR was performed on a 7500 Real-time PCR System (Applied Biosystems, Foster City, Calif.) using 1 µl of the first-strand cDNA product and SYBR_Premix Ex Taq™ (Takara Bio Inc., Shiga, Japan), according to the manufacturer's instructions. The technique is based on the ability to detect the RT-PCR product directly with no downstream processing. This was accomplished by monitoring the increase in fluorescence of a dye-labeled DNA probe specific for each factor under study, plus a probe specific for the 36B4 gene, which is used as an endogenous control for the assay. At this time the primers listed in Table 1 were used. PCR conditions were 50° C. for 2 minutes, 95° C. for 2 minutes, followed by 40 cycles at 95° C. for 15 seconds and 60° C. for 1 minute. Data were analyzed using the 2-DDCT method; data were presented as the fold in gene expression normalized to 36B4 and relative to UV-irradiated or control cells. These experiments were performed in triplicate and independently repeated at least three times.

TABLE 1

| Gene | Primer | Sequence (5'-3') | SEQ. ID. NO |
|---|---|---|---|
| 36B4 | Forward primer | TGGGCTCCAAGCAGATGC | 9 |
| | Reverse primer | GGCTTCGCTGGCTCCCAC | 10 |
| MMP-1 | Forward primer | ATTCTACTGATATCGGGGCTTTGA | 11 |
| | Reverse primer | ATGTCCTTGGGGTATCCGTGTAG | 12 |

As a result, as shown in Example <3-1>, MMP-1 gene expression was significantly increased in the UV-irradiated group, compared with the UV-non-irradiated group. In each group irradiated with UV and treated with the peptide, MMP-1 gene expression was reduced the peptide dose-dependently (FIG. 1a and FIG. 1b). Therefore, the TRPV1 inhibitory peptides of the present invention were confirmed to be able to reduce MMP-1 expression induced by UV.

<3-3> Confirmation of Proinflammatory Cytokine Expression

To investigate the changes of cytokine expression by TRPV1 inhibitory peptides in UV-irradiated cells, the expressions of IL-1β, IL-6, IL-8 and TNF-α in HaCaT cells treated with each TRPV1 inhibitory peptide were measured by the same manner as described in Example <3-1>.

As a result, the TRPV1 inhibitory peptides of the present invention were confirmed to reduce the expressions of the said cytokines which were increase by UV exposure (FIG. 2a~FIG. 2h).

EXAMPLE 4

Confirmation of Inhibitory Activity of TRPV1 Inhibitory Peptide on Capsaicin-Induced $Ca^{2+}$ Influx HaCaT cells were cultured on cover glasses, then loaded with 4 mM Fluo-4 AM (Molecular Probes) in serum-free medium at room temperature for 45 minutes. After washing three times with serum-free medium, the cells on the cover glasses were transferred to custom-built observation chambers, and allowed to accommodate for 20 minutes. In order to induce TRV1 activity, the cells were treated with capsaicin alone or capsaicin and the peptide of the present invention at the final concentration of 10 mM in Tyrode's buffer (140 mM NaCl, 5 mM KCl, 1 mM $MgCl_2$, 2 mM $CaCl_2$, 10 mM glucose, and 10 mM HEPES [pH 7.2]) for 3 minutes. The fluorescence intensity was measured using a confocal laser scanning microscope (LSM 510 META, Zeiss) fitted with appropriate filters and a PL Fluotar objective (200_, 0.5 NA) that was controlled by SCAN Ware 5.10 software (Zeiss). The experiments were performed at 37° C. in a humidified chamber. The $Ca^{2+}$ measurements lasted for 20 min, with images taken every 1 or 4 seconds.

Figure 3:
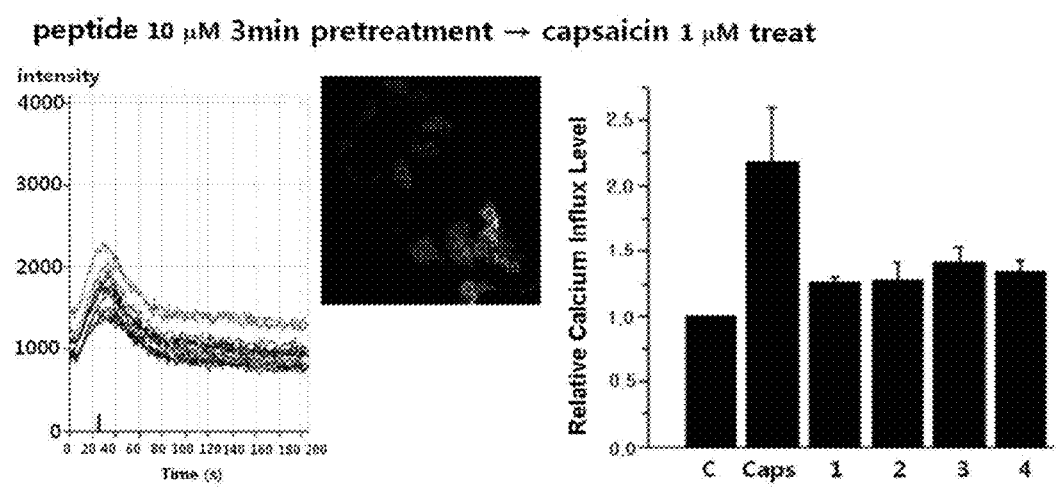
FIG. 3 is a diagram illustrating the changes of $Ca^{2+}$ influx induced by capsaicin by TRPV1 inhibitory peptide.

As a result, $Ca^{2+}$ strength was significantly low in the group treated with the TRPV1 inhibitory peptide, compared with the group treated with capsaicin alone without the peptide. Therefore, the TRPV1 inhibitory peptides of the present invention were confirmed to inhibit $Ca^{2+}$ influx in keratinocytes (FIG. 3).

EXAMPLE 5

UV Irradiation and Peptide Treatment to Mouse

<5-1> Mouse Raise and UV Irradiation

To confirm the inhibitory activity of TRPV1 inhibitory peptide on skin-aging in vivo, six-week-old female albino hairless mice (Skh-1) were acclimated for 1 week prior to the experiment and provided with food and water freely. All experimental protocols were approved by the Committee for Animal Care and Use at Seoul National University. For UV exposure, F75/85W/UV21 fluorescent sunlamps with an emission spectrum between 275 and 380 nm (peak at 310-315 nm) served as the UV source. A Kodacel filter (TA401/407; Kodak, Rochester, N.Y.) was mounted in front of the UV tube for removal of wavelengths of 290 nm. Irradiation intensity at the skin surface was measured using a UV meter (model 585100; Waldmann Co., Villingen-Schwenningen, Germany). The irradiation intensity 30 cm from the light source was 1.0 mW/$cm^2$. The present inventors initially measured the minimal erythema dose (MED)

on the dorsal skin of mice. MED is defined as the minimum amount of radiation required to produce an erythema with sharp margins after 24 hours. UV was exposed to the dorsal skin of hairless mice (Skh-1) in 2MED (1MED=100 mJ/cm$^2$).

<5-2> TRPV-1 Inhibitory Peptide Treatment

Figure 4:
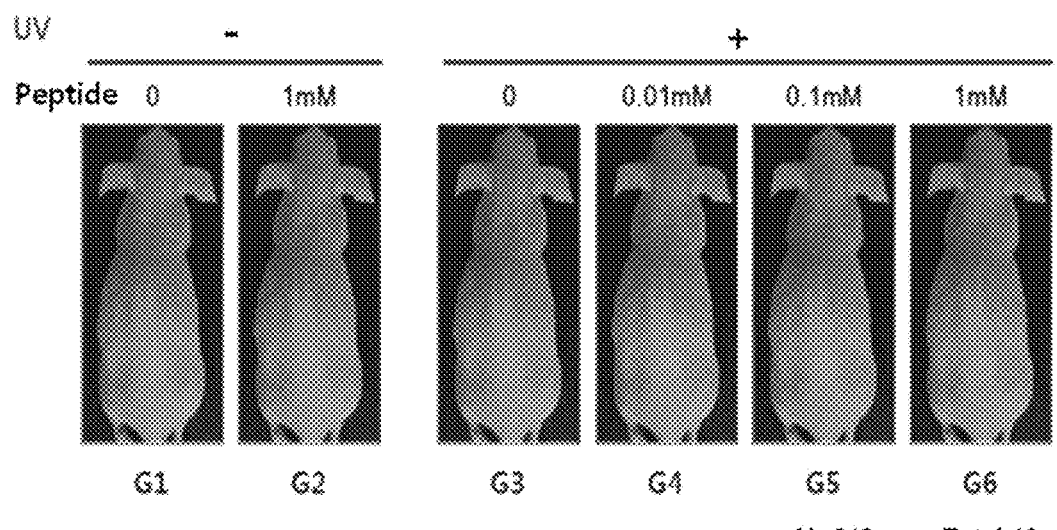
FIG. 4 is a diagram illustrating the treatment method of TRPV1 inhibitory peptide to nude mouse skin.

The Skh-1 mice were divided into six groups as follows: (1) UV-unexposed and vehicle-treated group, (2) UV-unexposed and 1 mM peptide-treated group, (3) UV-irradiated and vehicle-treated group, (4) UV-irradiated and 0.01 mM peptide-treated group, (5) 0.1 mM peptide-treated group, and (6) UV-irradiated and 1 mM peptide-treated group. Vehicle was composed of ethanol (30%) and polyethylene glycol (70%). Vehicle and peptide were applied to the dorsal skin surface at 0 and 24 h after UV irradiation. These mice were killed at 48 h after UV irradiation and skin specimens were biopsied (FIG. 4).

EXAMPLE 6

Confirmation of Decrease of Skinfold Thickness by TRPV1 Inhibitory Peptide

Using a caliper (PEACOCK, Ozaki MFG Co. Ltd., Tokyo, Japan), skinfold thickness was measured at 24 h before UV irradiation and 48 h after UV irradiation performed in Example <5-2>. Particularly, midline skin was manually pinched upward at the neck and at the base of the tail, and skinfold thickness was then measured mid-way between the neck and hips.

Figure 5:
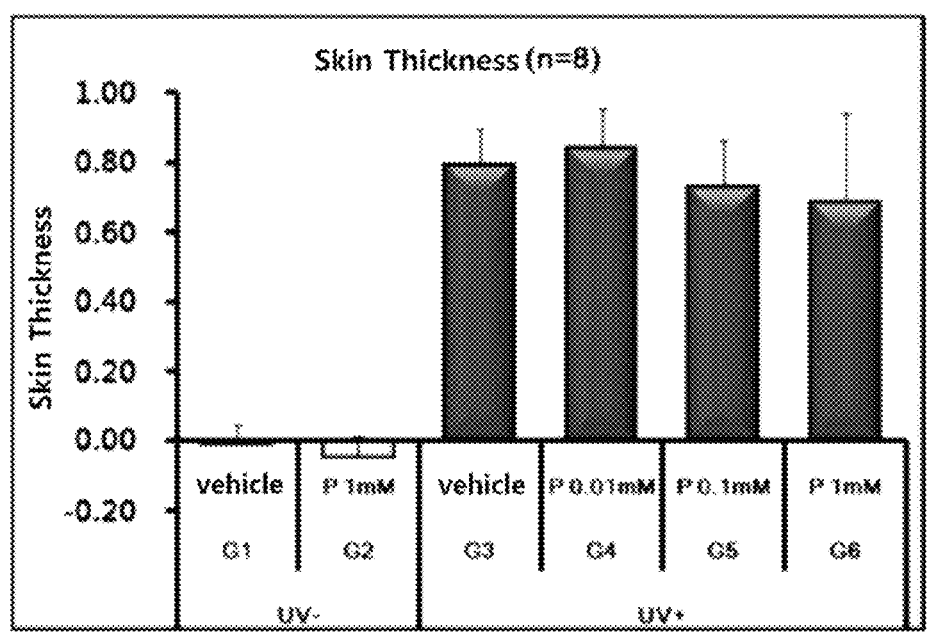
FIG. 5 is a diagram illustrating the changes of skinfold thickness of nude mouse increased by UV by TRPV1 inhibitory peptide.

As a result, skinfold thickness was rapidly increased by UV irradiation. However, when 1 mM of the TRPV1 inhibitory peptide was treated, the increased skinfold thickness was reduced (FIG. 5).

EXAMPLE 7

Confirmation of Inhibitory Activity of TRPV1 Inhibitory Peptide on UV-Induced MMP Expression In Vivo <7-1> Confirmation of MMP-13 Expression by Western Blotting Skin tissues of mice of Example <5-2> were homogenized in ice-cold lysis buffer [50 mM Tris-HCl, pH 7.4, 150 mM NaCl, 2 mM ethylenediamine tetra acetic acid (EDTA), 5 mM phenylmethanesulfonyl fluoride (PMSF), and 1 mM dithiothreitol (DTT), 1% Triton X-100] with freshly added protease inhibitor cocktail (Roche, Indianapolis, Ind.). Homogenates were then centrifuged at 15,000 g for 30 minutes at 4° C., and supernatants were then collected and stored at −70° C. Protein contents in lysates were determined using the Bradford assay. Equal amounts of protein were resolved over 8-16% Tris-Glycine SDS-PAGE gels, and then electrophoretically transferred to PVDF membranes. Blots were subsequently blocked with blocking buffer for 1 h at room temperature and incubated with monoclonal anti-MMP-13 antibody (Neomarkers, Fremont, Calif.). As a control, the corresponding β-actin levels were determined in the same cell lysates using antibodies for β-actin (Santa Cruz Biotechnology, Santa Cruz, Calif.). Signal strengths were quantified using a densitometric program.

Figure 6:
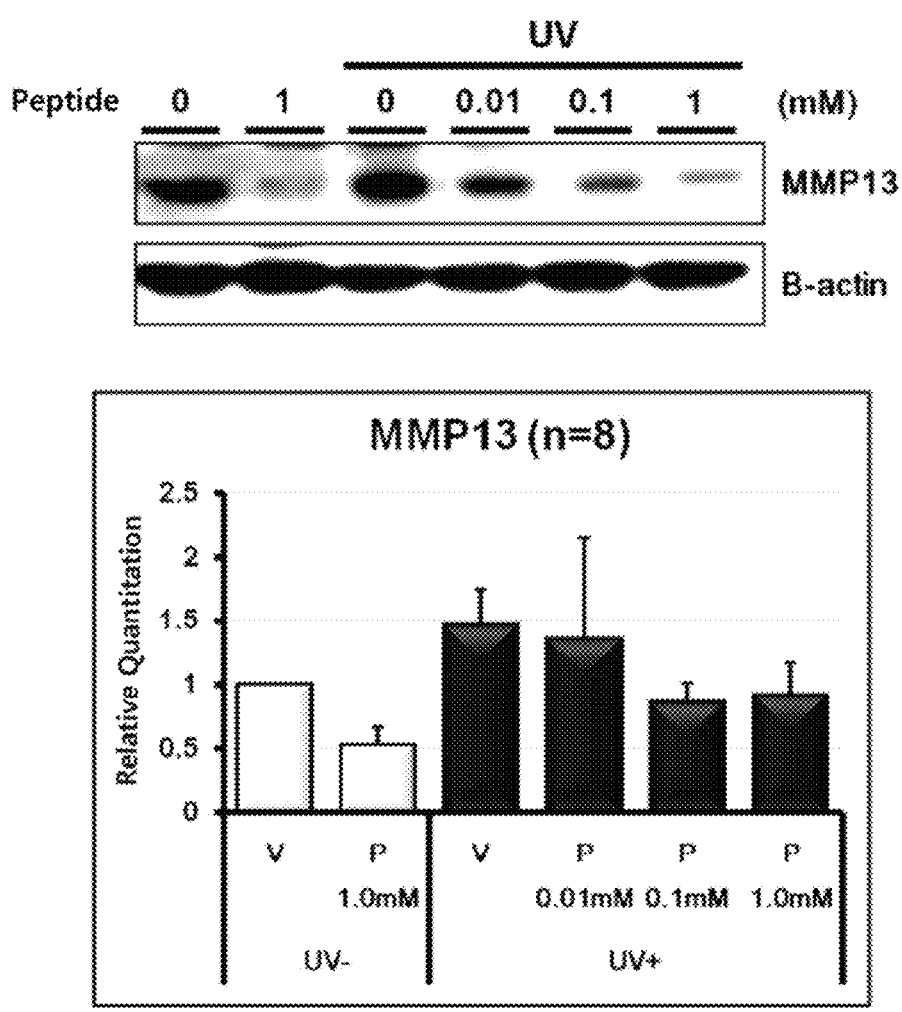
FIG. 6 is a diagram illustrating the changes of MMP-13 expression in nude mouse skin induced by UV by TRPV1 inhibitory peptide.

As a result, MMP-13 protein expression was increased in the UV-irradiated group, compared with the UV-non-irradiated group. In the meantime, MMP-13 protein expression was significantly reduced in the UV-irradiated and the peptide treated group the peptide dose-dependently (FIG. 6).

<7-2> Confirmation of MMP and Procollagen Gene Expressions by qRT-PCR

Total RNA was extracted from skin tissues of mice of Example <5-2> by the same method as described in Example <3-2>, and then cDNA was synthesized. For quantitative estimation of MMP mRNA expression, PCR was performed on a 7500 Real-time PCR System (Applied Biosystems, Foster City, Calif.) using SYBR_Premix Ex Taq™ (Takara Bio Inc., Shiga, Japan), according to the manufacturer's instructions. At this time the primers listed in Table 2 were used. PCR conditions were 50° C. for 2 minutes, 95° C. for 2 minutes, followed by 40 cycles at 95° C. for 15 seconds and 60° C. for 1 minute. Data were analyzed using the 2-DDCT method; data were presented as the fold in gene expression normalized to 37B4 and relative to UV-irradiated or control group. These experiments were performed in triplicate and independently repeated at least three times.

TABLE 2

| Gene | primer | Sequence (5'-3') | SEQ. ID. NO |
|---|---|---|---|
| Mouse 36B4 | forward primer | TGGGCTCCAAGCAGATGC | 9 |
|  | reverse primer | GGCTTCGCTGGCTCCCAC | 10 |
| Mouse MMP-13 | forward primer | CATCCATCCCGTGACCTTAT | 13 |
|  | reverse primer | GCATGACTCTCACAATGCGA | 14 |
| Mouse MMP-9 | forward primer | TTGAGTCCGGCAGACAATCC | 15 |
|  | reverse primer | CCTTATCCACGCGAATGACG | 16 |
| Mouse procollagen | forward primer | TCGTGACCGTGACCTTGCG | 17 |
|  | reverse primer | GAGGCACAGACGGCTGAGTAG | 18 |

Figure 7:
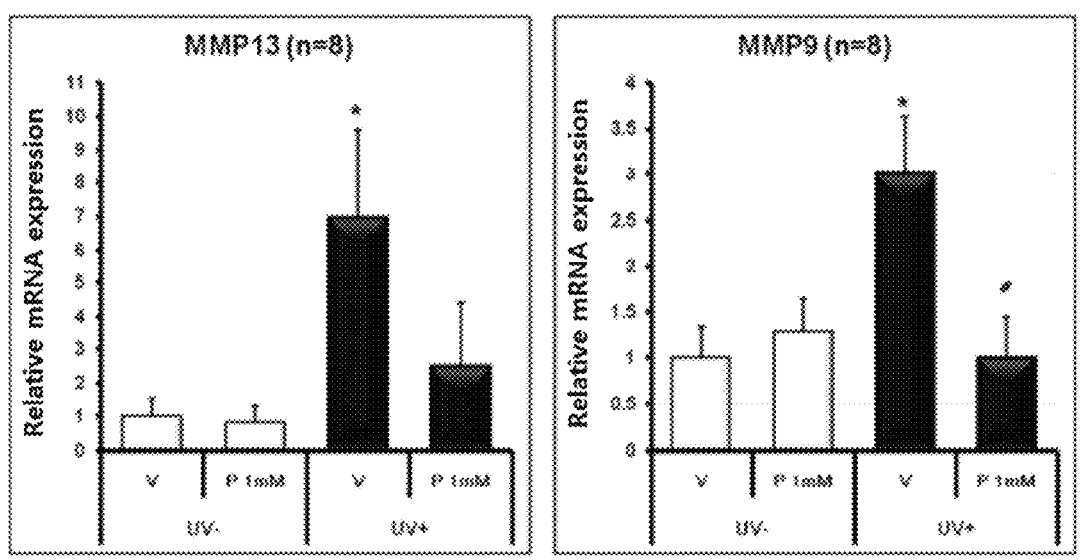
FIG. 7 is a diagram illustrating the changes of MMP-13 and MMP-9 gene expressions in nude mouse skin induced by UV by TRPV1 inhibitory peptide.
Figure 8:
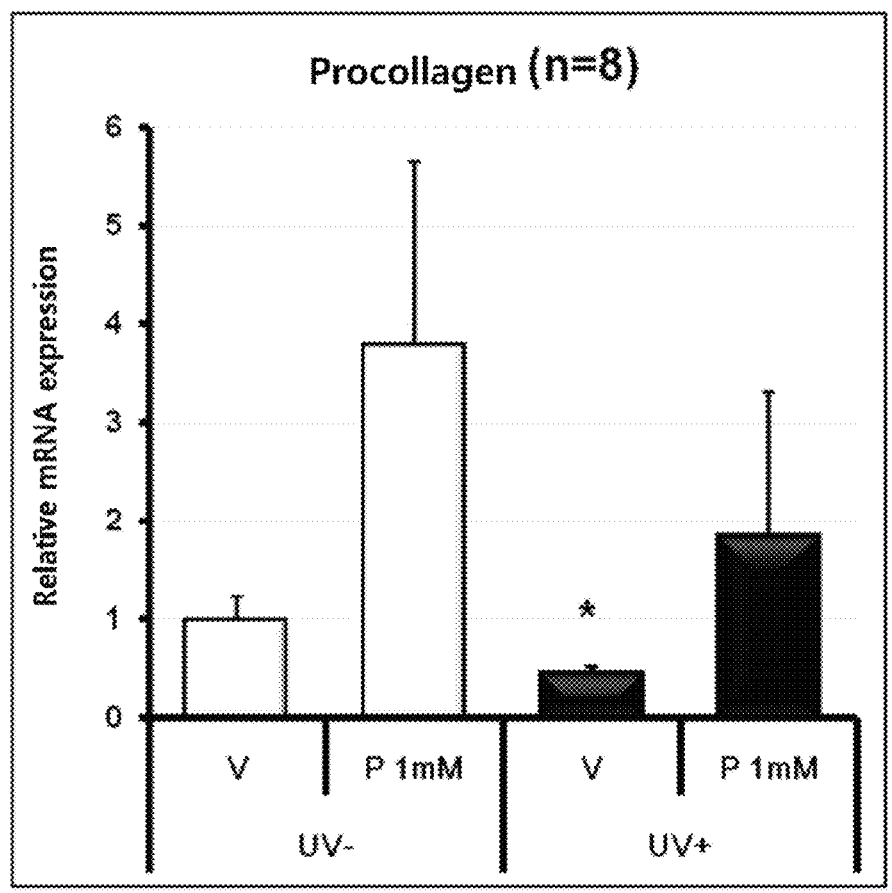
FIG. 8 is a diagram illustrating the changes of procollagen gene expression in nude mouse skin decreased by UV by TRPV1 inhibitory peptide.

As a result, the TRPV1 inhibitory peptides were confirmed to reduce significantly the expressions of MMP-13 and MMP-9 genes which were increased by UV exposure (FIG. 7). In the meantime, the expression of procollagen gene which was reduced by UV irradiation was significantly increased by the TRPV1 inhibitory peptides (FIG. 8).

EXAMPLE 8

Confirmation of Decrease of Skinfold Thickness Increased by UV by TRPV1 Inhibitory Peptide In order to measure the changes of skinfold thickness by TRPV1 inhibitory peptide, hematoxylin and eosin (H&E) staining was performed with mouse skin tissues of Example <5-2>. Particularly, mouse skin samples were fixed in 10% buffered formalin for 24 hours, and embedded in paraffin. Serial sections (4 μm) were mounted onto silane-coated slides, and stained with hematoxylin solutions for nuclear staining and eosin solutions for cytoplasm by routine methods as previously described. Epidermal thickness was measured using an image analysis program (BMI plus software, BumMi Universe Co., Kyungki, Korea).

Figure 9:
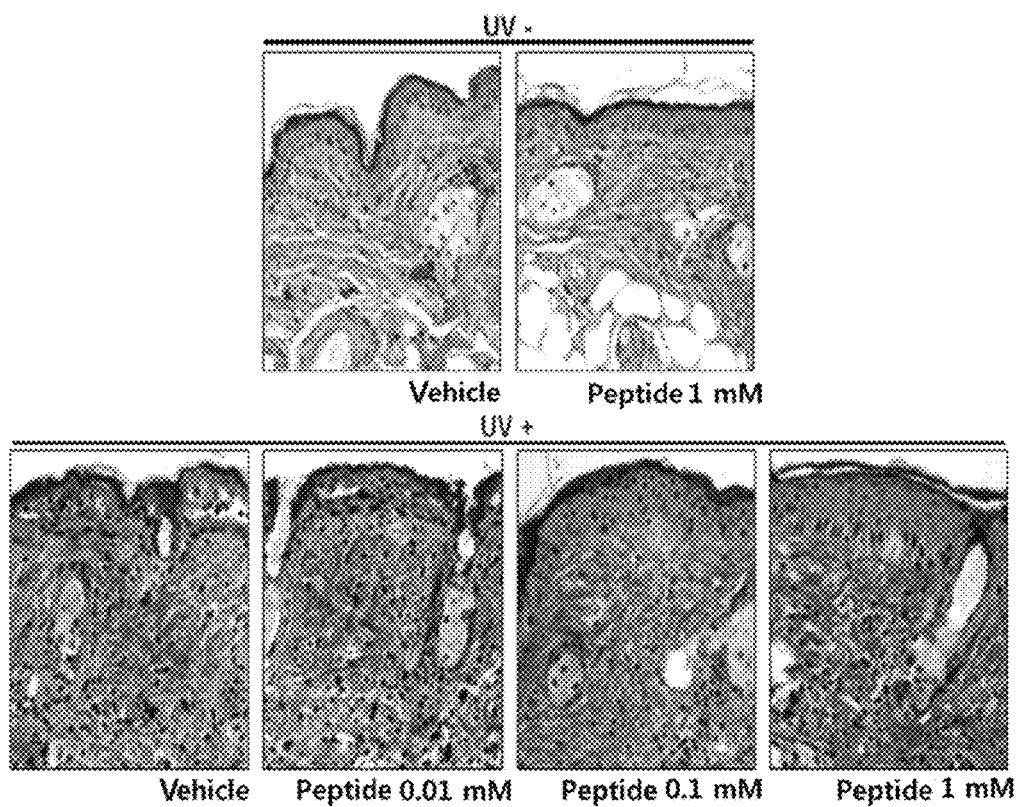
FIG. 9 is a diagram illustrating the changes of skinfold thickness of nude mouse increased by UV by TRPV1 inhibitory peptide.

As a result, mouse skinfold thickness was increased by UV irradiation. In the UV-irradiated and the peptide treated group, the increased skinfold thickness was reduced by the peptide treatment (FIG. 9).

EXAMPLE 9

Confirmation of Inhibitory Effect of TRPV1 Inhibitory Peptide on Apoptosis Induced by UV To confirm the inhibitory effect of TRPV1 inhibitory peptide on apoptosis induced by UV exposure, TUNEL staining was performed with mouse skin tissues. Particularly, mouse skin tissues were fixed in 10% buffered formalin for 24 hours, and embedded in paraffin. Serial sections (4 μm) were mounted onto silane-coated slides. In order to confirm apoptosis, general TUNEL staining was performed with Millipore™ (see the website at www dot millipore dot com slash userguides dot nsf slash a73664f9f981af8c852569b9005b4eee slash c60bd329d558cd0e852577d80069e1d0 slash $FILE slash S7101MAN dot pdf) using ApopTagPlus Peroxidase In Situ Apoptosis Kit.

Figure 10:
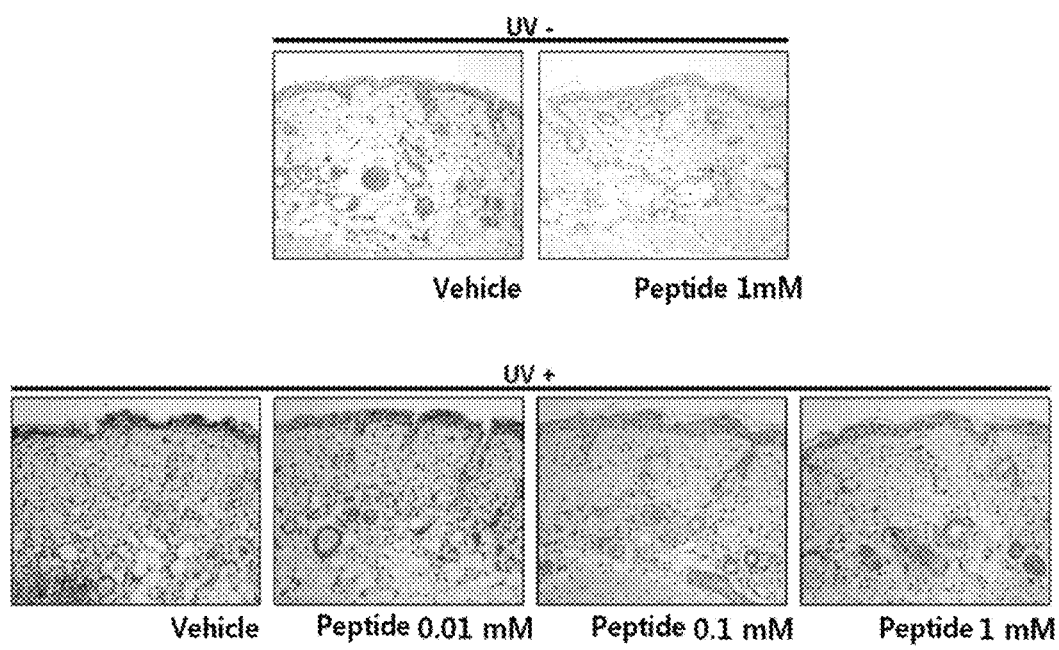
FIG. 10 is a diagram illustrating the changes of apoptosis in nude mouse skin increased by UV by TRPV1 inhibitory peptide.

As a result, apoptosis in skin tissues was increased by UV exposure, but the said peptide inhibited such increase of apoptosis effectively (FIG. 10).

Manufacturing Example 1

Preparation of Cosmetics

<1-1> Preparation of Skin Toner

Toner comprising the TRPV1 inhibitory peptide of the present invention as an active ingredient was prepared according to the composition shown in Table 3.

TABLE 3

| Constituent | Content (weight part) |
| --- | --- |
| Peptide 1 of Example 1 | 10.00 |
| 1,3-butylene glycol | 1.00 |
| Disodium EDTA | 0.05 |
| Allantoin | 0.10 |
| Dipotassium glycyrrhizate | 0.05 |
| Citric acid | 0.01 |
| Sodium citrate | 0.02 |
| Glycereth-26 | 1.00 |
| Arbutin | 2.00 |
| Hydrogenated castor oil | 1.00 |
| Ethanol | 30.00 |
| Preservative | Small amount |
| Stain | Small amount |
| Aromatics | Small amount |
| Purified water | Proper amount |

<1-2> Preparation of Nourishing Cream

Nourishing cream comprising the TRPV1 inhibitory peptide of the present invention as an active ingredient was prepared according to the composition shown in Table 4.

TABLE 4

| Constituent | Content (weight part) |
| --- | --- |
| Peptide 2 of Example 1 | 10.0 |
| 1,3-butyleneglycol | 7.0 |
| Glycerine | 1.0 |
| D-panthenol | 0.1 |

TABLE 4-continued

| Constituent | Content (weight part) |
| --- | --- |
| Plant extract | 3.2 |
| Magnesium aluminum silicate | 0.3 |
| PEG-40 stearate | 1.2 |
| Stearic acid | 2.0 |
| Polysorbate 60 | 1.5 |
| Glyceryl stearate, lipophilic | 2.0 |
| Sorbitan sesquioleate | 1.5 |
| Cetearyl alcohol | 3.0 |
| Mineral oil | 4.0 |
| Squalane | 3.8 |
| Caprlic/capric triglyceride | 2.8 |
| Vegitable oil | 1.8 |
| Dimethicone | 0.4 |
| Dipotassium glycyrrhizate | Small amount |
| Allantoin | Small amount |
| Sodium hyaluronate | Small amount |
| Tocopheryl acetate | Proper amount |
| Triethanolamine | Proper amount |
| Preservative | Proper amount |
| Aromatics | Small amount |
| Purified water | Proper amount |

<1-3> Preparation of Lotion

Lotion comprising the TRPV1 inhibitory peptide of the present invention as an active ingredient was prepared according to the composition shown in Table 5.

TABLE 5

| Constituent | Content (weight part) |
| --- | --- |
| Cetostearyl alcohol | 1.6 |
| Stearic acid | 1.4 |
| Glyceryl monostearate, lipophilic | 1.8 |
| PEG-100 stearate | 2.6 |
| Sorbitan sesquioleate | 0.6 |
| Squalene | 4.8 |
| Macadamia oil | 2 |
| Jojoba oil | 2 |
| Tocopherol acetate | 0.4 |
| Methylpolysiloxane | 0.2 |
| Ethylparaben | 0.1 |
| Tocopherol acetate | 0.4 |
| Methylpolysiloxane | 0.2 |
| Ethylparaben | 0.1 |
| Propyl paraben | 0.1 |
| 1,3-butyleneglycol | 4 |
| Methylparaben | 0.1 |
| Xanthan gum | 0.1 |
| Glycerine | 4 |
| D-panthenol | 0.15 |
| Allantoin | 0.1 |
| Peptide 3 of Example 1 | 3.5 |
| Carbomer (2% aq. Sol) | 4 |
| Triethanolamine | 0.15 |
| Ethanol | 3 |
| pt 41891 | 0.1 |
| p-H20 | 48.3 |

Manufacturing Example 2

Preparation of Pharmaceutical Formulations

<2-1> Preparation of Powders

| | |
| --- | --- |
| TRPV1 inhibitory peptide | 2 g |
| Lactose | 1 g |

Powders were prepared by mixing all the above components, which were filled in airtight packs according to the conventional method for preparing powders.

<2-2> Preparation of Tablets

| TRPV1 inhibitory peptide | 100 mg |
|---|---|
| Corn starch | 100 mg |
| Lactose | 100 mg |
| Magnesium stearate | 2 mg |

Tablets were prepared by mixing all the above components by the conventional method for preparing tablets.

<2-3> Preparation of Capsules

| TRPV1 inhibitory peptide | 100 mg |
|---|---|
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<2-4> Preparation of Pills

| TRPV1 inhibitory peptide | 1 g |
|---|---|
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<2-5> Preparation of Granules

| TRPV1 inhibitory peptide | 150 mg |
|---|---|
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

<2-6> Preparation of Injectable Solutions

| TRPV1 inhibitory peptide | 10 μg/ml |
|---|---|
| Weak HCl BP | until pH 3.5 |
| Injectable NaCl BP | up to 1 ml |

The TRPV1 inhibitory peptide of the present invention was dissolved in proper volume of injectable NaCl BP. pH of the prepared solution was regulated as 3.5 by using weak HCl BP. The volume was adjusted by using injectable NaCl BP. The solution was well mixed and filled in 5 ml type I transparent glass ampoules. The ampoules were sealed by melting the glass of opening, followed by autoclave at 120° C. for at least 15 minutes for sterilization.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A peptide for inhibiting transient receptor potential vanilloid type 1 (TRPV1) activity, as set forth by SEQ ID NO: 1.

2. A cosmetic composition for decreasing signs of skin-aging and wrinkle improvement comprising one or more peptide selected from the group consisting of the peptides as set forth by SEQ ID NO: 1 and SEQ ID NO: 3 as an active ingredient, wherein the peptide is in a concentration of 0.001~20 mM.

3. The cosmetic composition according to claim 2 formulated in one form selected from the group consisting of toner, essence, lotion, cream, pack, gel, ointment, patch, and spray.

4. A pharmaceutical composition for decreasing signs of skin-aging and wrinkle improvement comprising one or more of the peptides selected from the group consisting of the peptides as set forth by SEQ ID NO: 1 and SEQ ID NO: 3 as an active ingredient, wherein the peptide is in a concentration of 0.001~20 mM.

5. A pharmaceutical composition for alleviating inflammation, irritation, or pain comprising one or more of the peptides selected from the group consisting of the peptides as set forth by SEQ ID NO: 1 and SEQ ID NO: 3 as an active ingredient, wherein the peptide is in a concentration of 0.001~20 mM.

6. A method for decreasing signs of skin-aging and wrinkle improvement comprising administering a cosmetically effective dose of one or more of the peptides selected from the group consisting of the peptides as set forth by SEQ ID NO: 1 and SEQ ID NO: 3 to a subject in need thereof.

7. A method for skin whitening comprising administering a cosmetically effective dose of one or more of the peptides selected from the group consisting of the peptides as set forth by SEQ ID NO: 1 and SEQ ID NO: 3 to a subject in need thereof.

8. A method for decreasing signs of skin-aging and wrinkle improvement comprising administering a pharmaceutically effective dose of one or more of the peptides selected from the group consisting of the peptides as set forth by SEQ ID NO: 1 and SEQ ID NO: 3 to a subject in need thereof.

9. A method for skin whitening comprising administering a pharmaceutically effective dose of one or more of the peptides selected from the group consisting of the peptides as set forth by SEQ ID NO: 1 and SEQ ID NO: 3 to a subject in need thereof.

10. A method for alleviating inflammation, irritation, or pain comprising administering a pharmaceutically effective dose of one or more of the peptides selected from the group consisting of the peptides as set forth by SEQ ID NO: 1 and SEQ ID NO: 3 to a subject in need thereof.

11. A screening method of a TRPV1 inhibitor comprising the following steps:
 1) constructing a transformant by transfecting host cells with a plasmid containing polynucleotide encoding TRPV1;
 2) treating the transformant with TRPV1 specific activator and TRPV1 inhibitor candidate materials (experimental group), and treating the transformant with the said TRPV1 specific activator and one of peptides selected from the group consisting of the peptide as set forth by SEQ ID NO: 1 and SEQ ID NO: 3 (control group);
 3) measuring the activities of TRPV1 ion channels of the experimental group and the control group of step 2); and,
 4) comparing the results of both groups of step 3) and selecting TRPV1 inhibitor candidate materials demonstrating lower or similar TRPV1 ion channel activity to that of the control.

12. The screening method according to claim 11, wherein the TRPV1 specific activator is UV or capsaicin.

13. The screening method according to claim 11, wherein the measurement of TRPV1 ion channel activity is performed by calcium imaging.

14. A screening method of a candidate material for decreasing signs of skin-aging and wrinkle improvement comprising the following steps:
- 1) constructing a transformant by transfecting host cells with a plasmid containing polynucleotide encoding TRPV1;
- 2) treating the transformant with TRPV1 specific activator and test materials (experimental group), and treating the transformant with the said TRPV1 specific activator and one of peptides selected from the group consisting of the peptide as set forth by SEQ ID NO: 1 and SEQ ID NO: 3 (control group);
- 3) measuring the activities of TRPV1 ion channels of the experimental group and the control group of step 2); and,
- 4) comparing the results of both groups of step 3) and selecting test materials demonstrating lower or similar TRPV1 ion channel activity to that of the control.

15. The screening method according to claim 14, wherein the TRPV1 specific activator is UV or capsaicin.

16. The screening method according to claim 14, wherein the measurement of TRPV1 ion channel activity is performed by calcium imaging.

* * * * *